United States Patent [19]

Allais et al.

[11] 4,397,856
[45] Aug. 9, 1983

[54] ANALGESIC 4-HYDROXY-3-QUINOLINECARBOXAMIDES

[75] Inventors: André Allais, Gagny; François Clemence, Paris; Roger Deraedt, Pavillons sous Bois; Odile Lemartret, Paris, all of France

[73] Assignee: Roussel Uclaf, Paris, France

[21] Appl. No.: 262,952

[22] Filed: May 12, 1981

[30] Foreign Application Priority Data

May 19, 1980 [FR] France ............................ 80 11100

[51] Int. Cl.³ .................... A61K 31/47; C07D 215/56
[52] U.S. Cl. .................................. 424/251; 424/258; 544/328; 544/331; 546/156
[58] Field of Search ............... 546/156; 424/258, 251; 544/328, 331

[56] References Cited

U.S. PATENT DOCUMENTS 3,992,540 11/1976 Clemence et al. ............... 424/258
4,107,310 8/1978 Allais et al. ...................... 424/258
4,299,831 11/1981 Clemence et al. ............... 424/251

FOREIGN PATENT DOCUMENTS 12639 6/1980 European Pat. Off. ........... 424/258
2377400 9/1978 France ............................ 424/258
874980 8/1961 United Kingdom ............. 546/159

Primary Examiner—Donald G. Daus
Assistant Examiner—Diana G. Rivers
Attorney, Agent, or Firm—Hammond & Littell, Weissenberger and Muserlian

[57] ABSTRACT

Novel compounds of the formula

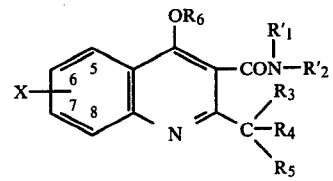

wherein X is in the 5,6,7 or 8 position and is selected from the group consisting of hydrogen, halogen, alkyl of 1 to 5 carbon atoms, alkoxy of 1 to 4 carbon atoms, $CF_3O—$, $CF_3S—$ and $CF_3—$, $R_1'$ is selected from the group consisting of hydrogen and alkyl of 1 to 4 carbon atoms, $R_2'$ is selected from the group consisting of hydrogen or an optionally unsaturated ring able to contain one or more heteroatoms of the group consisting of —S—, —O— and —N— optionally substituted with one or more members of the group consisting of (a) halogens, (b) alkyl of 1 to 4 carbon atoms optionally substituted with $NH_2$, $—NHAlK$ or $—N—(AlK)_2$ and AlK is alkyl of 1 to 3 carbon atoms, (c) phenyl, (d) alkoxy of 1 to 4 carbon atoms, (e) —OH, (f) —$CF_3$ and (g) —$NO_2$ or $R_1'$ together with the nitrogen atom to which they are attached form an optionally unsaturated ring, the said ring then being connected to the nitrogen atom by a double bond, $R_3$ is selected from the group consisting of hydrogen, halogen and alkyl of 1 to 4 carbon atoms, $R_4$ is selected from the group consisting of hydrogen and halogen, $R_5$ is a halogen with the proviso that $R_3$, $R_4$ and $R_5$ can not all be fluorine and $R_6$ is selected from the group consisting of hydrogen, alkyl of 1 to 8 carbon atoms and an acyl of an organic carboxylic acid of 2 to 8 carbon atoms and their non-toxic, pharmaceutically acceptable acid addition salts and their salts with non-toxic, pharmaceutically acceptable bases having a remarkable analgesic activity, a very weak anti-inflammatory activity and a good tolerance by the gastrointestinal system and their preparation and their intermediates.

27 Claims, No Drawings

ANALGESIC 4-HYDROXY-3-QUINOLINECARBOXAMIDES

STATE OF THE ART

U.S. Pat. Nos. 3,992,540 and No. 4,107,310 and copending, commonly assigned U.S. patent application Ser. No. 97,711 filed Nov. 27, 1979, now U.S. Pat. No. 4,299,831, describe 3-quinoline-carboxamides which differ from the compounds of the invention by their substitution in the 2-position. The compounds of U.S. Pat. No. 3,992,540 are unsubstituted in the 2-position while the compounds of U.S. Pat. No. 4,107,310 are substituted in the 2-position with an alkyl group. The compounds of application Ser. No. 97,711 are substituted in the 2-position with a —$CF_3$ group.

OBJECTS OF THE INVENTION

It is an object of the invention to provide the novel compounds of formula I' and their salts with acids and bases and a novel process for their preparation and novel intermediates therefor.

It is another object of the invention to provide novel analgesic compositions and to a novel method of relieving pain in warm-blooded animals.

These and other objects and advantages of the invention will become obvious from the following detailed description.

THE INVENTION

The novel 4-hydroxy-3-quinoline-carboxamides of the invention are selected from the group consisting of compounds of the formula

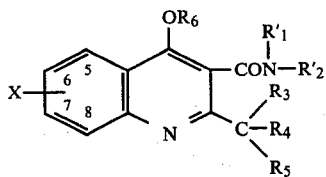

I' wherein X is in the 5,6,7 or 8 position and is selected from the group consisting of hydrogen, halogen, alkyl of 1 to 5 carbon atoms, alkoxy of 1 to 4 carbon atoms, $CF_3O$—, $CF_3S$— and $CF_3$—, $R_1'$ is selected from the group consisting of hydrogen and alkyl of 1 to 4 carbon atoms, $R_2'$ is selected from the group consisting of hydrogen or an optionally unsaturated ring able to contain one or more heteroatoms of the group consisting of —S—, —O— and —N— optionally substituted with one or more members of the group consisting of (a) halogens, (b) alkyl of 1 to 4 carbon atoms optionally substituted with $NH_2$, —NHAlK or —N—(AlK)$_2$ and AlK is alkyl of 1 to 3 carbon atoms, (c) phenyl, (d) alkoxy of 1 to 4 carbon atoms, (e) —OH, (f) —$CF_3$ and (g) —$NO_2$ or $R_1'$ and $R_2'$ together with the nitrogen atom to which they are attached form an optionally unsaturated ring, the said ring then being connected to the nitrogen atom by a double bond, $R_3$ is selected from the group consisting of hydrogen, halogen and alkyl of 1 to 4 carbon atoms, $R_4$ is selected from the group consisting of hydrogen and halogen, $R_5$ is a halogen with the proviso that $R_3$, $R_4$ and $R_5$ can not all be fluorine and $R_6$ is selected from the group consisting of hydrogen, alkyl of 1 to 8 carbon atoms and an acyl of an organic carboxylic acid of 2 to 8 carbon atoms and their non-toxic, pharmaceutically acceptable acid addition salts and their salts with non-toxic, pharmaceutically acceptable bases.

When $R_1'$ is alkyl, it is preferably methyl or ethyl and when X is an halogen, it is preferably chlorine although it may be fluorine, bromine or iodine. When X is alkyl, it is preferably methyl, ethyl, n-propyl, n-butyl, n-pentyl, isopropyl or isobutyl. When X is alkoxy, it is preferably methoxy, ethoxy or n-propoxy.

When $R_2'$ is a ring, it is preferably thiazolyl, phenyl, pyridinyl, thienyl, benzothiazolyl, oxazolyl or imidazolyl. When $R_2'$ is a substituted ring, the substituents are preferably selected from the group consisting of chlorine, methyl, ethyl, dimethylaminomethyl, phenyl, methoxy, ethoxy, —OH, —$CF_3$ and —$NO_2$.

When $R_3$ is alkyl, it is preferably methyl or ethyl and when $R_3$ is halogen, it is preferably fluorine, chlorine or bromine. $R_4$ is preferably fluorine, chlorine or bromine and $R_5$ is preferably chlorine or bromine. When $R_6$ is alkyl, it is preferably methyl or ethyl and when $R_6$ is acyl, it is preferably derived from an aliphatic carboxylic acid such as acetic acid, propionic acid or butynyl carboxylic acid.

Example of suitable acids to form the non-toxic, pharmaceutically acceptable acid addition salts are mineral acids such as hydrochloric acid, hydrobromic acid, sulfuric acid and phosphoric acid and organic acids such as acetic acid, citric acid, oxalic acid, formic acid, alkylsulfonic acids such as methanesulfonic acid or ethanesulfonic acid or arylsulfonic acids such as p-toluenesulfonic acid or benzenesulfonic acid.

Examples of suitable non-toxic, pharmaceutically acceptable salts formed with bases are alkali metal salts such as sodium and potassium and amines such as trimethylamine and dimethylamine.

Among the preferred compounds of the invention are those of the formula

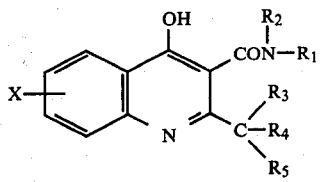

I wherein X, $R_3$, $R_4$ and $R_5$ have the above definition, $R_1$ is selected from the group consisting of hydrogen and alkyl of 1 to 4 carbon atoms, $R_2$ is selected from the group consisting of thiazolyl, 4,5-dihydrothiazolyl, pyridinyl, oxazolyl, isoxazolyl, imidazolyl, pyrimidyl and tetrazolyl all optionally substituted with alkyl of 1 to 4 carbon atoms and phenyl optionally substituted with at least one member of the group consisting of —OH, alkyl of 1 to 4 carbon atoms, alkoxy of 1 to 4 carbon atoms, halogen, —$CF_3$ and —$NO_2$ and their non-toxic, pharmaceutically acceptable salts of acids and bases.

Particularly preferred compounds of formula I are those wherein $R_3$ is hydrogen, alkyl or the same halogen as $R_5$, those wherein $R_4$ is hydrogen or the same halogen as $R_5$, those wherein X is —$CF_3$, those wherein $R_1$ is hydrogen, those wherein $R_3$ and $R_4$ are individually hydrogen or chlorine and $R_5$ is chlorine and those wherein

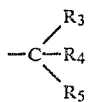

is —CHCl$_2$ and their non-toxic, pharmaceutically acceptable salts with acids or bases.

Preferably R$_2$ is thiazolyl and the most preferred compound of formula I' is 2-dichloromethyl-4-hydroxy-N-(2-thiazolyl)-8-trifluoromethyl-3-quinoline-carboxamide and its non-toxic, pharmaceutically acceptable salts with acids and bases.

The novel process of the invention for the preparation of the compounds of formula I' comprises reacting a compound of the formula

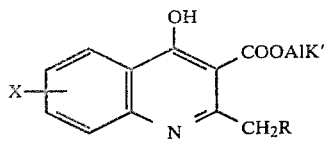

wherein X has the above definition, Alk' is alkyl of 1 to 8 carbon atoms and R is selected from the group consisting of hydrogen and alkyl of 1 to 4 carbon atoms with a halogenation agent and then with a halogenation agent different from the first to obtain a compound of the formula

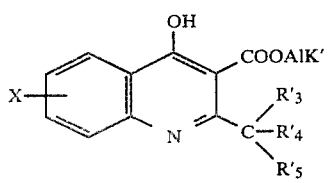

wherein R$_3$', R$_4$' and R$_5$' have the same definition of as R$_3$, R$_4$ and R$_5$, respectively, and, if desired, reacting the compound of formula III$_A$ with a compound of formula Hal$_1$—M wherein Hal$_1$ is a halogen and M is an alkali metal to obtain a compound of the formula

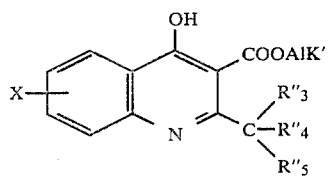

wherein R$_3$" is selected from the group consisting of hydrogen, Hal$_1$ and alkyl of 1 to 4 carbon atoms, R$_4$" is selected from the group consisting of hydrogen and Hal$_1$ and R$_5$ is Hal$_1$, reacting either compound III$_A$ or III$_B$ with a saponification agent to obtain a compound of the formula

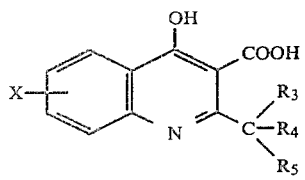

optionally transforming the said acid into a functional derivative thereof, reacting the acid of formula IV or its functional derivative with a compound of the formula

wherein R$_1$' and R$_2$' have the above definitions to obtain a compound of the formula

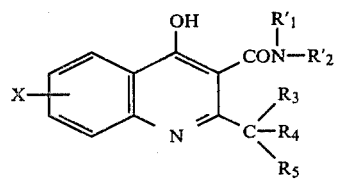

which is a compound of formula I' wherein R$_6$ is hydrogen and optionally reacting the latter with an etherification agent or esterification agent to obtain a compound of the formula

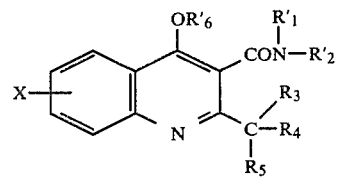

wherein R$_6$' is selected from the group consisting of alkyl of 1 to 8 carbon atoms and acyl of an organic carboxylic acid of 2 to 8 carbon atoms which is a compound of formula I' wherein R$_6$ is other than hydrogen and optionally reacting the compounds of formula I$_A$' or I$_B$' with a non-toxic, pharmaceutically acceptable acid or base to form the corresponding salt.

A preferred mode of the said process comprises reacting a compound of the formula

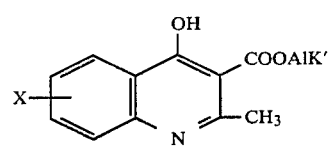

wherein X and Alk' have the above definitions with a halogenation agent to obtain a compound of the formula

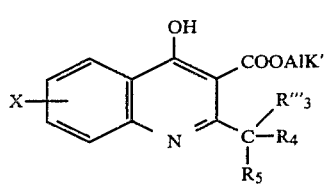

wherein R$_3$''' and R$_4$ are selected from the group consisting of hydrogen and the same halogen as R$_5$, reacting the latter with a saponification agent to obtain a compound of the formula

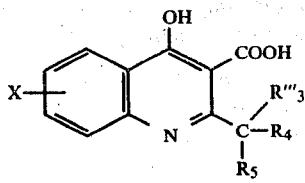

optionally transforming the said acid into a functional derivative thereof, reacting the acid of formula $IV_a$ or its functional derivative with a compound of formula V to obtain a compound of the formula

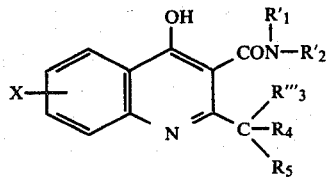

which is a compound of formula I' wherein $R_6$ is hydrogen and $R_3$ has the values of $R_3'''$, optionally reacting the latter with an etherification agent or an esterification agent to obtain a compound of the formula

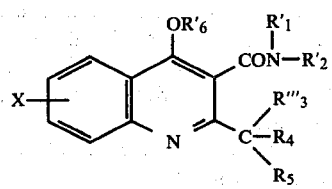

which is a compound of formula I' wherein $R_6$ is other than hydrogen and $R_3$ is $R_3'''$ and optionally reacting a compound of formula $I_C'$ or $I_D'$ with a non-toxic, pharmaceutically acceptable acid or base to form the corresponding salt.

Examples of suitable halogenation agents are the halogens, cupric halides and N-bromo or N-chloro-amides such as N-bromo-succinimide, N-chloro-succinimide, N-bromo-acetamide and N-chloro-acetamide. To obtain mono, di- or tri-halo compounds, different quantities of the halogenation agents are used.

Examples of functional acid derivatives are the acid chloride, lower alkyl esters, its anhydride and mixed anhydrides. The condensation of the acid or its functional derivative with the amine of formula V is effected in an inert organic solvent such as benzene, toluene, pyridine or ethyl acetate in the presence of a basic agent such as triethylamine. The etherification or esterification of the compounds of formulae $I_A'$ and $I_C'$ may be effected by known methods.

In a preferred mode of the said process of the invention, AlK' is methyl or ethyl and the halogenation agent is a N-haloamide such as N-chloro-acetamide, N-bromo-acetamide, N-chloro-succinimide or N-bromo-succinimide with the reaction being effected in a solvent such as carbon tetrachloride, chloroform or acetic acid in the presence of a radical initiator such as light, azobisisobutyronitrile or a peroxide such as benzoyl peroxide. $Hal_1$ is preferably fluorine and M is preferably potassium. The saponification agent is sodium hydroxide or potassium hydroxide. The most preferred halogenation agents are N-bromo-succinimide or N-chloro-succinimide.

In a modification of the process of the invention, a compound of formulae $III_A$, $III_B$ or $III_a$ is reacted with a compound of formula V in the presence of a trialkylaluminum to obtain a compound of formula $I_A'$ or $I_C'$ which can then be reacted further. The trialkylaluminum is preferably trimethylaluminum or triisobutylaluminum.

Another process of the invention for the preparation of a compound of formula I' comprises reacting a compound of the formula

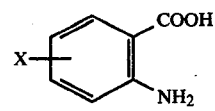

wherein X has the above definition with an acid of the formula

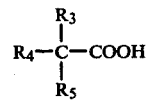

wherein $R_3$, $R_4$ and $R_5$ have the above definition or a functional derivative thereof to obtain a compound of the formula

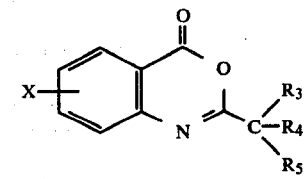

reacting the latter with a compound of the formula

wherein $R_1'$ and $R_2'$ have the above definition to obtain a compound of the formula

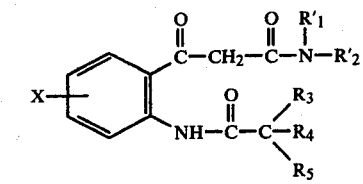

cyclizing the latter in the presence of an alkaline agent to obtain a compound of formula $I_A'$ which can be reacted with an etherification agent or esterification agent to form the compound of formula $I_B'$ and optionally reacting the compound of formula $I_A'$ or $I_B'$ with a non-toxic, pharmaceutically acceptable acid or base to form the corresponding salt.

In a preferred embodiment of the said process, the functional derivative of the acid of formula VII is the acid halide or anhydride. The reaction of the compounds of formulae VIII and IX is preferably effected in the presence of an organolithium such as butyllithium or a lithium amide such as lithiumdiisopropylamide. The cyclization of the compound of formula X is effected in the presence of an alkali metal hydride such as sodium hydride, an alkali metal carbonate such as sodium carbonate or potassium carbonate or an amine such as piperidine, 4-amino-pyridine, triethylamine, 1,5-diazabicyclo[4,3,0]-non-5-ene, 1,4-diazabicyclo[2,2,2]octane or 1,5-diazabicyclo[5,4,0]undec-5-ene.

The starting materials of formulae II and VI are generally known products and may be prepared by the processes described in French Pat. No. 2,340,735 and No. 2,157,874.

The novel intermediate compounds of the invention are the compounds of formulae $III_A$, $III_B$, IV, VIII and X and especially those of formulae $III_a$ and $IV_a$.

The novel analgesic compositions of the invention are comprised of an analgesically effective amount of at least one compound of formula I' and their non-toxic, pharmaceutically acceptable salts with acids and bases and a pharmaceutical carrier or excipient. The compositions may be in the form of tablets, dragees, gelules, granules, suppositories, injectable solutions or suspensions, pomades, cremes, gels or aerosol preparations.

Examples of suitable excipients are talc, arabic gum, lactose, starch, magnesium stearate, cacao butter, aqueous or non-aqueous vehicles, fatty bodies of animal or vegetable origin, paraffinic derivatives, glycols, diverse wetting agents, emulsifiers or dispersants and preservatives.

The said compositions have an excellent analgesic activity, a very weak anti-inflammatory activity and are well tolerated in the gastrointestinal tract. The compositions therefore are useful for treatment of muscular, articular or nervous pain, dental pain, migraines as well as for rheumatic affections.

The novel method of the invention for relieving pain in warm-blooded animals, including humans, comprises administering to warm-blooded animals an analgesically effective amount of at least one compound of formula I' and their non-toxic, pharmaceutically acceptable salts with acids and bases. The compounds may be administered orally, rectally, parenterally or topically on the skin or mucous. The effective dose will vary depending on the compound, the cause of pain and the method of administration but the preferred effective daily oral dose is 0.4 to 40 mg/kg.

In the following examples there are described several preferred embodiments to illustrate the invention. However, it should be understood that the invention is not intended to be limited to the specific embodiments.

EXAMPLE 1

2-(dichloromethyl)-4-hydroxy-N-(2-thiazolyl)-8-trifluoromethyl-3-quinoline-carboxamide-PROCEDURE A STEP A: Ethyl 2-dichloromethyl-4-hydroxy-8-trifluoromethyl-3-quinoline-carboxylate A mixture of 11.92 g of ethyl 2-methyl-4-hydroxy-8-trifluoromethyl-3-quinoline-carboxylate, 400 ml of carbon tetrachloride, 13.30 g of N-chloro-succinimide and 600 mg of benzoyl peroxide was refluxed for 24 hours and was then cooled to room temperature and filtered. The filtrate was evaporated to dryness to obtain 17 g of an oil which was chromatographed over silica gel. Elution with methylene chloride yielded 13.6 g of a product melting at 80° to 85° C. which was empasted with petroleum ether (b.p.=60°–80° C.) and was vacuum filtered. The product was rinsed and dried to obtain 8.8 g of ethyl 2-dichloromethyl-4-hydroxy-8-trifluoromethyl-3-quinoline-carboxylate melting at 88° C.

STEP B:
2-dichloromethyl-4-hydroxy-8-trifluoromethyl-3-quinoline-carboxylic acid A solution of 22 g of the product of Step A, 220 ml of ethanol and 110 ml of sodium hydroxide was stirred at room temperature for 36 hours and the ethanol was then evaporated at less than 40° C. under reduced pressure. The solution was diluted with 200 ml of water and ice and the pH was adjusted to 1 by addition of concentrated hydrochloric acid. The mixture was vacuum filtered and the product was washed with water and then was dissolved in ether. The solution was filtered and the filtrate was dried and evaporated to dryness under reduced pressure to obtain 18 g of 2-dichloromethyl-4-hydroxy-8-trifluoromethyl-3-quinoline-carboxylic acid which was used as is for the next step.

STEP C:
2-dichloromethyl-4-hydroxy-N-(2-thiazolyl)-8-trifluoromethyl-3-quinoline-carboxamide A solution of 15 g of the product of Step B, 400 ml of anhydrous benzene and 16 ml of thionyl chloride was refluxed for 90 minutes and then the benzene and excess thionyl chloride were removed by distillation under reduced pressure to obtain 2-dichloromethyl-4-hydroxy-N-(2-thiazolyl)-8-trifluoromethyl-3-quinoline-carboxylic acid chloride.

A solution of the said product in 120 ml of ethyl acetate was admixed with stirring under an inert atmosphere with a solution of 4.41 g of 2-amino-thiazole, 50 ml of anhydrous ethyl acetate and 18.5 ml of triethylamine and the mixture was refluxed for one hour and stood overnight at room temperature. The mixture was filtered and the filtrate was washed with aqueous sodium chloride to avoid emulsions, dried and evaporated to dryness under reduced pressure. The residue was solidified in 150 ml of 20% hydrochloric acid and the mixture was vacuum filtered. The product was washed with water until the wash water was neutral and was dissolved damp in 50 ml of N sodium hydroxide solution. The solution was filtered and the filtrate was acidified to a pH of 4–5 with 50% hydrochloric acid. The mixture was iced and was vacuum filtered. The product was washed with water and dried under reduced pressure at 90° C. to obtain 8.5 g of raw product which was crystallized from ethyl acetate to obtain 5.7 g of 2-dichloromethyl-4-hydroxy-N-(2-thiazolyl)-8-trifluoromethyl-3-quinoline-carboxamide melting at 204° C.

EXAMPLE 2

2-dichloromethyl-4-hydroxy-N-phenyl-8-trifluoromethyl-3-quinoline-carboxamide-PROCEDURE B 17.5 ml of a 25% solution of trimethylaluminum in hexane were added at 15° to 18° C. to a solution of 3.72 g of aniline in 100 ml of methylene chloride and after stirring the mixture for 15 minutes, 7.56 g of the product of Step A of Example 1 were added thereto at the same temperature. The mixture was refluxed for 22 hours and was then poured into 100 ml of an iced 20% aqueous hydrochloric acid solution. The decanted aqueous phase was extracted with ethyl acetate and the combined organic phases were washed with water, dried and evaporated to dryness. The crystalline residue was empasted with ether, filtered, dried and crystallized from ethyl acetate to obtain 1.1 g of 2-dichloromethyl-4-hydroxy-N-phenyl-8-trifluoromethyl-3-quinoline-carboxamide which after crystallization from ethanol melted at 200°–202° C. (decomposition).

Analysis: $C_{18}H_{11}N_2O_2Cl_2F_3$; molecular weight=415.217. Calculated: %C 52.07; %H 2.67; %N 6.75; %Cl 17.08; %F 13.73; Found: C 52.0; H 2.6; N 6.7; Cl 17.4; F 13.6

EXAMPLE 3

2-dichloromethyl-4-hydroxy-N-(2-pyridinyl)-8-trifluoromethyl-3-quinoline-carboxamide Using the procedure of Example 2, 3.76 g of 2-aminopyridine and 7.36 g of the compound of Step A of Example 1 were reacted and the product was crystallized from ethyl acetate to obtain 2.7 g of 2-dichloromethyl-4-hydroxy-N-(2-pyridinyl)-8-trifluoromethyl-3-quinoline-carboxamide which after crystallization from methanol melted at 212° C. (decomposition).

Analysis: $C_{17}H_{10}N_3Cl_2F_3O_2$; molecular weight=416.199. Calculated: %C 49.06; %H 2.42; %N 10.10; %Cl 17.04; %F 13.69; Found: C 49.0; H 2.3; N 10.0; Cl 17.2; F 13.2

EXAMPLE 4

2-dichloromethyl-4-hydroxy-N-(2-thiazolyl)-8-trifluoromethyl-3-quinoline-carboxamide A solution of 30 ml of 25% trimethylaluminum in hexane and 30 ml of toluene was added at 5° C. to a solution of 13.75 g of 2-amino-thiazole in 150 ml of toluene and after stirring the mixture at 5° to 10° C. for 30 minutes, 9.2 g of the product of Step A of Example 1 were added thereto all at once. After gas evolution ceased, the mixture was heated at 80° to 85° C. under an inert gas for 3½ hours. The mixture was evaporated to dryness under reduced pressure and the residue was added to 500 ml of N hydrochloric acid. The mixture was stirred for one hour and was filtered. The filter was washed with water, then with a mixture of water and 2 N sodium hydroxide and finally with water and the combined alkaline phases were filtered and 2 N hydrochloric acid was slowly added to the filtrate until the pH was 5. The mixture was vacuum filtered and the product was washed with water and dried to obtain 7.48 g of raw product melting at ≈200° C. The product was crystallized from ethyl acetate with activated carbon treatment to obtain 4.19 g of 2-dichloromethyl-4-hydroxy-N-(2-thiazolyl)-8-trifluoromethyl-3-quinoline-carboxamide melting at 204° C. which was identical to the product of Example 1.

EXAMPLE 5

2-(1-chloroethyl)-4-hydroxy-N-(2-thiazolyl)-8-trifluoromethyl-3-quinoline-carboxamide STEP A: Ethyl 2-(1-chloroethyl)-4-hydroxy-8-trifluoromethyl-3-quinoline-carboxylate A mixture of 9.3 g of ethyl 2-ethyl-4-hydroxy-8-trifluoromethyl-3-quinoline-carboxylate, 200 ml of carbon tetrachloride, 4.2 g of N-chlorosuccinimide and 0.45 g of azobis-isobutyronitrile was stirred at 65° C. maximum for 5 hours under a lamp and was then cooled to 20° C. and was filtered. The filtrate was evaporated to dryness and the residue was taken up in methylene chloride. The mixture was washed with water, dried and evaporated to dryness. The residue was empasted with petroleum ether and dried to obtain 9 g of ethyl 2-(1-chloroethyl)-4-hydroxy-8-trifluoromethyl-3-quinoline-carboxylate melting at 104° C.

STEP B:
2-(1-chloroethyl)-4-hydroxy-N-(2-thiazolyl)-8-trifluoromethyl-3-quinoline-carboxamide Using the procedure of Example 4, 1.5 g of 2-aminothiazole and 1.041 g of the product of Step A were reacted and after the addition of N hydrochloric acid, the mixture was extracted with ethyl acetate. The organic phase was washed with water, dried and evaporated to dryness. The residue was chromatographed over silica gel and was eluted with ethyl acetate to obtain 2-(1-chloroethyl)-4-hydroxy-N-(2-thiazolyl)-8-trifluoromethyl-3-quinoline-carboxamide which after crystallization from ether melted at ≈190° C. (decomposition).

EXAMPLE 6

Using the procedure of Example 2, ethyl 2-dichloromethyl-4-hydroxy-8-trifluoromethyl-3-quinoline-carboxylate was reacted to obtain 2-dichloromethyl-4-hydroxy-N-(4-phenyl-2-thiazolyl)-8-trifluoromethyl-3-quinoline-carboxamide melting at 210° C. (decomposition).

EXAMPLE 7

Using the procedure of Example 2, ethyl 2-dichloromethyl-4-hydroxy-8-trifluoromethyl-3-quinoline-carboxylate was reacted to obtain 2-dichloromethyl-4-hydroxy-N-(5-methyl-2-thiazolyl)-8-trifluoromethyl-3-quinoline-carboxamide melting at 240°–250° C. (decomposition).

EXAMPLE 8

Using the procedure of Example 2, ethyl 2-dichloromethyl-4-hydroxy-8-trifluoromethyl-3-quinoline-carboxylate was reacted to obtain 2-dichloromethyl-4-hydroxy-N-(4,5-dihydroxy-2-thienyl)-8-trifluoromethyl-3-quinoline-carboxamide melting at ≈205° C. (decomposition).

EXAMPLE 9

Using the procedure of Example 2, ethyl 2-dichloromethyl-4-hydroxy-8-trifluoromethyl-3-quinoline-carboxylate was reacted to obtain 2-dichloromethyl-4-hydroxy-N-(2-benzothiazolyl)-8-trifluoromethyl-3-quinoline-carboxamide melting at ≈265° C. (decomposition).

EXAMPLE 10

Using the procedure of Example 1, ethyl 2-dichloromethyl-4-hydroxy-8-trifluoromethyl-3-quinoline-carboxylate was reacted to obtain 2-dichloromethyl-4-hydroxy-N-(2-thiazolyl)-8-trifluoromethyl-3-quinoline-carboxamide melting at 228°–230° C. (decomposition).

EXAMPLE 11

Using the procedure of Example 1, ethyl 2-dichloromethyl-4-hydroxy-8-trifluoromethyl-3-quinoline-carboxylate was reacted to obtain 2-dichloromethyl-4-hydroxy-N-(3-methyl-2-thiazolylidene)-8-trifluoromethyl-3-quinoline-carboxamide melting at 270°–280° C. (decomposition).

EXAMPLE 12

Using the procedure of Example 1, ethyl 2-dichloromethyl-4-hydroxy-8-trifluoromethyl-3-quinoline-carboxylate was reacted to obtain 2-dichloromethyl-4-hydroxy-N-(5-chloro-2-thiazolyl)-8-trifluoromethyl-3-quinoline-carboxamide melting at 245° C. (decomposition).

EXAMPLE 13

Using the procedure of Example 1, ethyl 2-dichloromethyl-4-hydroxy-8-trifluoromethyl-3-quinoline-carboxylate was reacted to obtain 2-dichloromethyl-4-hydroxy-N-(2-oxazolyl)-8-trifluoromethyl-3-quinoline-carboxamide melting at ≈220° C. (decomposition).

EXAMPLE 14

Using the procedure of Example 1, ethyl 2-dichloromethyl-4-hydroxy-8-trifluoromethyl-3-quinoline-carboxylate was reacted to obtain 2-dichloromethyl-4-hydroxy-N-(1-methyl-2-imidazolyl)-8-trifluoromethyl-3-quinoline carboxamide melting at 240° C. (decomposition).

EXAMPLE 15

Using the procedure of Example 1, ethyl 2-dichloromethyl-4-hydroxy-8-trifluoromethyl-3-quinoline-carboxylate was reacted to obtain 2-dichloromethyl-4-hydroxy-N-(4-dimethylamino-3-methyl-2-thiazolyl)-8-trifluoromethyl-3-quinoline carboxamide.

EXAMPLE 16

Using the procedure of Step A of Example 5, ethyl 2-methyl-4-hydroxy-8-trifluoromethyl-3-quinoline-carboxylate was chlorinated to obtain ethyl 2-chloromethyl-4-hydroxy-8-trifluoromethyl-3-quinoline-carboxylate which was then reacted as in Example 1 to obtain 2-chloromethyl-4-hydroxy-N-(2-thiazolyl)-8-trifluoromethyl-3-quinoline-carboxamide melting at 218° C. (decomposition).

EXAMPLE 17

Using the procedure of Step A of Example 5, ethyl 2-(1,1-dichloroethyl)-4-hydroxy-8-trifluoromethyl-3-quinoline-carboxylate was prepared and was then further reacted to obtain 2-(1,1-dichloroethyl)-4-hydroxy-N-(2-thiazolyl)-8-trifluoromethyl-3-quinoline-carboxamide melting at 220° C. (decomposition).

EXAMPLE 18

2-dichloromethyl-4-hydroxy-N-(2-thiazolyl)-8-trifluoromethyl-3-quinoline-carboxamide

STEP A:

2-dichloromethyl-8-trifluoromethyl-4H-3,1-benzoxazin-4-one

A mixture of 17.44 g of 2-amino-3-trifluoromethylbenzoic acid prepared by the process of J. Med. Chem., Vol. 16 (2) (1973), p. 101–106 and 34.63 g of dichloroacetyl chloride was progressively heated with stirring and at about 50° C., a hardening of the mass with rapid gas evolution of regular hydrogen chloride occured for one hour. Towards 100° C., one observed a fluidization of the reaction mixture, an intensification of hydrogen chloride evolution and an increase in the temperature of 127° C. The heating was continued until hydrogen chloride evolution ceased to obtain a brown solution which was cooled in an ice bath with stirring. The mixture was vacuum filtered and the product was empasted with ether, then with methanol and was washed with methanol to obtain 23.82 g of 2-dichloromethyl-8-trifluoromethyl-4H-3,1-benzoxazine-4-one melting at 179° C.

STEP B:

2-(dichloroacetylamino)-β-oxo-N-(2-thiazolyl)-3-trifluoromethyl-benzene-propanamide 87.7 ml of 1.1 mols of n-butyllithium per liter of hexane were added with stirring under nitrogen at −3° to −1° C. to a solution of 8.65 g of N-(2-thiazolyl)-acetamide and 304 ml of tetrahydrofuran and the mixture was stirred at −3° to −1° C. for 20 minutes and was then cooled to −75° C. A solution of 9.073 g of 2-dichloromethyl-8-trifluoromethyl-4H-3,1-benzoxazine-4-one in 95.5 ml of tetrahydrofuran was added with strong stirring to the mixture at −73° to −75° C. and the mixture was stirred at −75° C. for 2 hours to obtain a brown solution which was poured into a mixture of ice, water and hydrochloric acid. The mixture was vacuum filtered to obtain 935 mg of 2-(dichloroacetylamino)-β-oxo-N-(2-thiazolyl)-3-trifluoromethyl-benzene-propanamide melting at 223° C.

The aqueous phase was extracted with ethyl acetate and the organic phase was washed with water, dried and evaporated to dryness. The 15.2 g of residue were added to 100 ml of methylene chloride and the mixture was triturated and was vacuum filtered. The product was empasted with 30 ml of methylene chloride and the mixture was vacuum filtered. The product was washed with 10 ml of methylene chloride to obtain 7.47 g of the desired product melting at 223° C.

STEP C:

2-dichloromethyl-4-hydroxy-N-(2-thiazolyl)-8-trifluoromethyl-3-quinoline-carboxamide A solution of 8.81 g of the product of Step B in 100 ml of dimethylformamide was added to a suspension of 1.06 g of sodium hydride and 50 ml of dimethylformamide and the mixture was stirred at room temperature for 4 hours and was poured into an ice-water-hydrochloric acid mixture. The mixture was vacuum filtered and the product was washed with water and then dissolved in 300 ml of methylene chloride. The solution was washed with water, dried over magnesium sulfate and was filtered. The filtrate was evaporated to dryness and the 8.5 g of residue melting at 175° C. were triturated with ethanol and was vacuum filtered. The 6.95 g of product were crystallized from 215 ml of ethyl acetate to remove insoluble traces to obtain 5.015 g of 2-dichloromethyl-4-hydroxy-N-(2-thiazolyl)-8-trifluoromethyl-3-quinoline-carboxamide melting at 204° C.

The said process was repeated using potassium carbonate in place of sodium hydride to obtain the same product melting at 204° C.

EXAMPLE 19

2-chloromethyl-4-hydroxy-N-(2-thiazolyl)-8-trifluoromethyl-3-quinoline-carboxamide Using the procedure of Step A of Example 18, 2-amino-3-trifluoromethyl-benzoic acid and chloroacetyl chloride were reacted to obtain 2-chloromethyl-8-trifluoromethyl-4H-3,1-benzoxazine-3-one melting at 76°–78° C. which was then reacted with N-(2-thiazolyl)-acetamide by the process of Step B of Example 18 to obtain 2-(chloroacetylamino)-β-oxo-N-(2-thiazolyl)-3-trifluoromethyl-benzene-propanamide melting at 192°≈194° C.

The said product was reacted by the procedure of Step C of Example 18 with dimethylamino-pyridine in tetrahydrofuran to obtain 2-chloromethyl-4-hydroxy-N-(2-thiazolyl)-8-trifluoromethyl-3-quinoline-carboxamide melting at 218° C.

EXAMPLE 20

2-(1-chloroethyl)-4-hydroxy-N-(2-thiazolyl)-8-trifluoromethyl-3-quinoline-carboxamide Using the procedure of Step A of Example 18, 1-chloropropionyl chloride and 2-amino-3-trifluoromethylbenzoic acid were reacted to obtain 2-(1-chloroethyl)-8-trifluoromethyl-4H-3,1-benzoxazine-4-one melting at 112° C. which was reacted by the procedure of Step B of Example 18 with N-(2-thiazolyl)-acetamide to obtain 2-(1-chloropropionylamino)-β-oxo-3-trifluoromethyl-N-(2-thiazolyl)-benzene-propanamide melting at 215° C. The latter was reacted by the procedure of Step C of Example 18 to obtain 2-(1-chloroethyl)-4-hydroxy-N-(2-thiazolyl)-8-trifluoromethyl-3-quinoline-carboxamide melting at 190°–192° C.

EXAMPLE 21

2-(1,1-dichloroethyl)-4-hydroxy-N-(2-thiazolyl)-8-trifluoromethyl-3-quinoline-carboxamide Using the procedure of Step A of Example 18, 2-amino-3-trifluoromethyl-benzoic acid and dichloro-propionyl chloride were reacted to obtain 2-(1,1-dichloroethyl)-8-trifluoromethyl-4H-3,1-benzoxazin-4-one melting at 120° C. which was reacted with N-(2-thiazolyl)-acetamide by the procedure of Step B of Example 18 to obtain 2-(1,1-dichloropropionylamino)-β-oxo-N-(2-thiazolyl)-3-trifluoromethyl-benzene-propanamide melting at 136°–138° C.

The latter product was reacted by the procedure of Step C of Example 18 to obtain 2-(1,1-dichloroethyl)-4-hydroxy-N-(2-thiazolyl)-8-trifluoromethyl-3-quinoline-carboxamide melting at 220° C.

EXAMPLE 22

2-(difluoromethyl)-4-hydroxy-N-(2-thiazolyl)-8-trifluoromethyl-3-quinoline-carboxamide Using the procedure of Step A of Example 18, 2-amino-3-trifluoromethyl-benzoic acid and difluoroacetic acid anhydride were reacted to obtain 2-(difluoromethyl)-8-trifluoromethyl-4H-3,1-benzoxazin-4-one melting at 82° C. which was reacted with N-(2-thiazolyl)-acetamide by the procedure of Step B of Example 18 to obtain 2-(difluoroacetylamino)-β-oxo-3-trifluoromethyl-N-(2-thiazolyl)-benzene-propanamide melting at 206° C. The latter compound was reacted by the procedure of Step C of Example 18 to obtain 2-(difluoromethyl)-4-hydroxy-N-(2-thiazolyl)-8-trifluoromethyl-3-quinoline-carboxamide melting at 226° C.

EXAMPLE 23

2-dichloromethyl-4-hydroxy-N-(2-oxazolyl)-8-trifluoromethyl-3-quinoline-carboxamide Using the procedure of Step B of Example 18, 2-dichloromethyl-8-trifluoromethyl-4H-3,1-benzoxazin-4-one and N-(2-oxazolyl)-acetamide were reacted to obtain 2-(dichloroacetamido)-β-oxo-N-(2-oxazolyl)-3-trifluoromethyl-benzene-propanamide which was reacted by the procedure of Step C of Example 18 to obtain 2-dichloromethyl-4-hydroxy-N-(2-oxazolyl)-8-trifluoromethyl-3-quinoline-carboxamide melting at 220°–225° C.

EXAMPLE 24

2-dichloromethyl-4-hydroxy-N-(1-methyl-2-imidazolyl)-8-trifluoromethyl-3-quinoline-carboxamide Using the procedure of Step B of Example 18, 2-dichloromethyl-8-trifluoromethyl-4H-3,1-benzoxazin-4-one and N-(1-methyl-2-imidazolyl)-acetamide were reacted to obtain 2-(dichloroacetamido)-β-oxo-N-(1-methyl-2-imidazolyl)-3-trifluoromethyl-benzene-propanamide which was then reacted by the procedure of Step C of Example 18 to obtain 2-dichloromethyl-4-hydroxy-N-(1-methyl-2-imidazolyl)-8-trifluoromethyl-3-quinoline-carboxamide melting at ≈240° C. (decomposition).

EXAMPLE 25

Tablets were prepared containing 50 mg of 2-dichloromethyl-4-hydroxy-N-(2-thiazolyl)-8-trifluoromethyl-3-quinoline-carboxamide and sufficient excipient of lactose, starch, talc and magnesium stearate for a final tablet weight of 350 mg.

PHARMACOLOGICAL DATA

A. Analgesic Activity

The test used was that of Koster et al [Fed. Proc., Vol. 1B (1959), p. 412] in which the intraperitonal injection of acetic acid provokes in mice repeated stretching and twisting movements which persist for more than 6 hours. Analgesics diminish or prevent this syndrome which is considered to be an exteriorization of a diffuse abdominal pain. A solution of 1% acetic acid in water was used and the dose which gave rise to this syndrome was 0.01 ml/g or 100 mg/k of acetic acid under these conditions.

The test product was orally administered to the mice which were fasted for 24 hours before the test 30 minutes before the acetic acid injection and the stretchings were observed and counted for each mouse for an observation period of 15 minutes starting immediately after the acetic acid injection. The results expressed as $DA_{50}$ which is the dose which diminished by 50% the number of stretchings as compared to the control animals were 0.6 mg/kg for the compound of Example 1.

B. Anti-inflammatory Activity

The anti-inflammatory activity was determined by the planetary edema test provoked by carraghenine in rats. Male rats weighing about 130 to 150 g received 0.05 ml of a sterile 1% carraghenine suspension in tibiotarsien joint of a rear foot while simultaneously orally administering the compound of Example 1 in a suspension of 0.25% of carboxymethylcellulose and 0.02% Tween. The volume of the rear foot was measured before administration and 2, 4, 6, 8 and 24 hours after. The intensity of the inflammation was maximum 4 to 6 hours after the carraghenine administration and the difference in volume of the paws of the treated and the control animals was evidence of the anti-inflammatory activity of the test compound. The compound of Example 1 was inactive at a dose of 50 mg/kg.

Various modifications of the compounds and processes of the invention may be made without departing from the spirit or scope thereof and it should be understood that the invention is intended to be limited only as defined in the appended claims.

What we claim is:

1. A compound selected from the group consisting of compounds of the formula

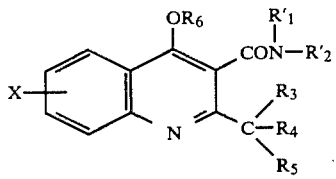

wherein X is the 5,6,7 or 8 position and is selected from the group consisting of hydrogen, halogen, alkyl of 1 to 5 carbon atoms, alkoxy of 1 to 4 carbon atoms, $CF_3O—$, $CF_3S—$ and $—CF_3—$, $R_1'$ is selected from the group consisting of hydrogen and alkyl of 1 to 4 carbon atoms, $R_2'$ is selected from the group consisting of hydrogen, thiazolyl, 4,5-dihydrazolyl, pyridinyl, oxazolyl, isoxazolyl, imidazolyl, pyrimidyl, tetrazolyl, thienyl, benzothiazolyl and phenyl, all optionally substituted with one or more members of the group consisting of (a) halogens, (b) alkyl of 1 to 4 carbon atoms optionally substituted with $NH_2$, $—NHAlK$ or $—N—(AlK)_2$ and AlK is alkyl of 1 to 3 carbon atoms, (c) phenyl, (d) alkoxy of 1 to 4 carbon atoms, (e) $—OH$, (f) $—CF_3$ and (g) $—NO_2$ or $R_1'$ and $R_2'$ together with the nitrogen atom to which they are attached form thiazolylidene, $R_3$ is selected from the group consisting of hydrogen, halogen and alkyl of 1 to 4 carbon atoms, $R_4$ is selected from the group consisting of hydrogen and halogen, $R_5$ is halogen with the proviso that $R_3$, $R_4$ and $R_5$ can not all be fluorine and $R_6$ is selected from the group consisting of hydrogen, alkyl of 1 to 8 carbon atoms and an acyl of an organic carboxylic acid of 2 to 8 carbon atoms and their non-toxic, pharmaceutically acceptable acid addition salts and their salts with non-toxic, pharmaceutically acceptable bases.

2. A compound of claim 1 wherein $R_6$ is hydrogen, $R_1'$ is selected from the group consisting of hydrogen and alkyl of 1 to 4 carbon atoms and $R_2'$ is selected from the group consisting of thiazolyl, 4,5-dihydrothiazolyl, pyridinyl, oxazolyl, isoxazolyl, imidazolyl, pyrimidyl and tetrazolyl all optionally substituted with alkyl of 1 to 4 carbon atoms and phenyl optionally substituted with at least one member of the group consisting of $—OH$, alkyl of 1 to 4 carbon atoms, alkoxy of 1 to 4 carbon atoms, halogen, $—CF_3$ and $—NO_2$.

3. A compound of claim 2 wherein $R_3$ is selected from the group consisting of hydrogen, alkyl of 1 to 4 carbon atoms and the same halogen as $R_5$ and $R_4$ is selected from the group consisting of hydrogen and the same halogen as $R_5$.

4. A compound of claim 2 wherein X is $—CF_3$.

5. A compound of claim 2 wherein $R_1$ is hydrogen.

6. A compound of claim 2 wherein $R_5$ is chlorine and $R_3$ and $R_4$ are individually selected from the group consisting of hydrogen and chlorine.

7. A compound of claim 6 wherein

is $—CHCl_2$.

8. A compound of claim 2 wherein $R_2$ is thiazolyl.

9. A compound of claim 1 which is 2-dichloromethyl-4-hydroxy-N-(2-thiazolyl)-8-trifluoromethyl-3-quinolinecarboxamide and its salts with non-toxic, pharmaceutically acceptable acids and bases.

10. An analgesic composition comprising an analgesically effective amount of at least one compound of claim 1 and a pharmaceutical carrier.

11. A composition of claim 10 wherein $R_6$ is hydrogen, $R_1'$ is selected from the group consisting of hydrogen and alkyl of 1 to 4 carbon atoms and $R_2'$ is selected from the group consisting of thiazolyl, 4,5-dihydrothiazolyl, pyridinyl, oxazolyl, isoxazolyl, imidazolyl, pyrimidyl and tetrazolyl all optionally substituted with alkyl of 1 to 4 carbon atoms and phenyl optionally substituted with at least one member of the group consisting of $—OH$, alkyl of 1 to 4 carbon atoms, alkoxy of 1 to 4 carbon atoms, halogen, $—CF_3$ and $—NO_2$.

12. A composition of claim 10 wherein $R_3$ is selected from the group consisting of hydrogen, alkyl of 1 to 4 carbon atoms and the same halogen as $R_5$ and $R_4$ is selected from the group consisting of hydrogen and the same halogen as $R_5$.

13. A composition of claim 10 wherein X is $—CF_3$.

14. A composition of claim 10 wherein $R_1$ is hydrogen.

15. A composition of claim 10 wherein $R_5$ is chlorine and $R_3$ and $R_4$ are individually selected from the group consisting of hydrogen and chlorine.

16. A composition of claim 10 wherein

is $—CHCl_2$.

17. A composition of claim 10 wherein $R_2$ is thiazolyl.

18. A composition of claim 10 wherein the compound is 2-dichloromethyl-4-hydroxy-N-(2-thiazolyl)-8-trifluoromethyl-3-quinoline-carboxamide and its salts with non-toxic, pharmaceutically acceptable acids and bases.

19. A method of relieving pain in warm-blooded animals comprising administering to warm-blooded animals an analgesically effective amount of at least one compound of claim 1.

20. A method of claim 19 wherein $R_6$ is hydrogen, $R_1'$ is selected from the group consisting of hydrogen and alkyl of 1 to 4 carbon atoms and $R_2'$ is selected from the group consisting of thiazolyl, 4,5-dihydrothiazolyl, pyridinyl, oxazolyl, isoxazolyl, imidazolyl, pyrimidyl and tetrazolyl all optionally substituted with alkyl of 1 to 4 carbon atoms and phenyl optionally substituted with at least one member of the group consisting of $—OH$, alkyl of 1 to 4 carbon atoms, alkoxy of 1 to 4 carbon atoms, halogen, $—CF_3$ and $—NO_2$.

21. A method of claim 19 wherein $R_3$ is selected from the group consisting of hydrogen, alkyl of 1 to 4 carbon atoms and the same halogen as $R_5$ and $R_4$ is selected from the group consisting of hydrogen and the same halogen as $R_5$.

22. A method of claim 19 wherein X is —$CF_3$.

23. A method of claim 19 wherein $R_1$ is hydrogen.

24. A method of claim 10 wherein $R_5$ is chlorine and $R_3$ and $R_4$ are individually selected from the group consisting of hydrogen and chlorine.

25. A method of claim 19 wherein

is —$CHCl_2$.

26. A method of claim 19 wherein $R_2$ is thiazolyl.

27. A method of claim 19 wherein the compound is 2-dichloromethyl-4-hydroxy-N-(2-thiazolyl)-8-trifluoromethyl-3-quinoline-carboxamide and its salts with non-toxic, pharmaceutically acceptable acids and bases.

* * * * *

UNITED STATES PATENT AND TRADEMARK OFFICE
CERTIFICATE OF CORRECTION

PATENT NO. : 4,397,856

DATED : August 9, 1983

INVENTOR(S) : ANDRÉ ALLAIS ET AL.

It is certified that error appears in the above-identified patent and that said Letters Patent is hereby corrected as shown below:

Title page, line 15 of Abstract after structural formula, "$R_1$' together" should read -- $R_1$' and $R_2$' together --.

Column 6, line 5: "trialkyla-" should read -- trialkyl- --.

Column 6, line 6: "luminum" should read -- aluminum --.

Column 10, line 6; Column 13, lines 26 and 33:

"chloroe-" should read -- chloro- --.

Column 10, line 7; Column 13, lines 27, 34; Column 13, line 43:

"thyl" should read -- ethyl --.

Column 13, line 42: "dichloroe-" should read -- dichloro --.

Column 15, first line after formula: "is the" should read

-- is in the --.

UNITED STATES PATENT AND TRADEMARK OFFICE
CERTIFICATE OF CORRECTION

PATENT NO.  : 4,397,856  
DATED       : August 9, 1983  
INVENTOR(S) : ANDRÉ ALLAIS ET AL.

Page 2 of 2

It is certified that error appears in the above-identified patent and that said Letters Patent is hereby corrected as shown below:

Column 17, claim 24: "A method of claim 10" should read

-- A method of claim 19 --.

Signed and Sealed this

Eighteenth Day of September 1984

[SEAL]

Attest:

GERALD J. MOSSINGHOFF

Attesting Officer

Commissioner of Patents and Trademarks